(12) United States Patent
Wu et al.

(10) Patent No.: US 10,116,262 B2
(45) Date of Patent: Oct. 30, 2018

(54) FRONT-END AMPLIFIER CIRCUITS FOR BIOMEDICAL ELECTRONICS

(71) Applicant: Winbond Electronics Corp., Taichung (TW)

(72) Inventors: Chung-Yu Wu, Hsinchu (TW); Ya-Syuan Sung, Taipei (TW)

(73) Assignee: WINBOND ELECTRONICS CORP., Taichung (TW)

( * ) Notice: Subject to any disclaimer, the term of this patent is extended or adjusted under 35 U.S.C. 154(b) by 1 day.

(21) Appl. No.: 15/383,261

(22) Filed: Dec. 19, 2016

(65) Prior Publication Data

US 2017/0272036 A1  Sep. 21, 2017

(30) Foreign Application Priority Data

Mar. 16, 2016 (CN) .......................... 2016 1 0150167

(51) Int. Cl.
*H03F 3/45* (2006.01)
*H03F 1/02* (2006.01)
(Continued)

(52) U.S. Cl.
CPC ....... *H03F 1/0205* (2013.01); *A61B 5/04004* (2013.01); *A61B 5/0428* (2013.01); *H03F 1/08* (2013.01); *H03F 3/187* (2013.01); *H03F 3/45071* (2013.01); *H03F 3/45197* (2013.01); *H03F 3/45973* (2013.01); *H03F 3/68* (2013.01); *H03F 3/72* (2013.01); *H03G 1/0029* (2013.01); *H03G 1/0088* (2013.01); *H03G 3/001* (2013.01); *H03G 3/3005* (2013.01); *H03G 3/3084* (2013.01); *H03G 5/28* (2013.01); *H03H 11/0422* (2013.01); *H03F 2200/261* (2013.01);
(Continued)

(58) Field of Classification Search
CPC .... H03F 3/45; H03F 3/45179; H03F 3/45183; H03F 3/45188; H03F 3/08; H03F 3/085; H03G 1/0047; H03G 3/3084
USPC .......................................................... 330/253
See application file for complete search history.

(56) References Cited

U.S. PATENT DOCUMENTS 5,392,000 A * 2/1995 Gillig ...................... H03F 1/083
                                                                    330/107
7,518,453 B2 * 4/2009 Segarra .................. G01R 19/32
                                                                    330/254
(Continued)

FOREIGN PATENT DOCUMENTS

WO    WO 2006/073463 A2    7/2006

OTHER PUBLICATIONS

Reid R. Harrison, Member, IEEE, and Cameron Charles,Low-Power Low-Noise CMOS Amplifier for Neural Recording Applications, IEEE Journal of Solid-State Circuits,Jun. 2003,pp. 958-965 vol. 38, No. 6,IEEE, Salt Lake City, UT.
(Continued)

*Primary Examiner* — Khanh V Nguyen
(74) *Attorney, Agent, or Firm* — Muncy, Geissler, Olds & Lowe, P.C.

(57) ABSTRACT

A front-end amplifier circuit for receiving a biological signal includes a signal channel. The signal channel amplifies the biological signal to generate a detection current and includes a capacitive-coupled transconductance amplifier. The capacitive-coupled transconductance amplifier amplifies the biological signal with a transconductance gain to generate a first current.

16 Claims, 10 Drawing Sheets

(51) Int. Cl.
*A61B 5/04* (2006.01)
*A61B 5/0428* (2006.01)
*H03F 3/187* (2006.01)
*H03F 3/68* (2006.01)
*H03G 3/30* (2006.01)
*H03H 11/04* (2006.01)
*H03F 1/08* (2006.01)
*H03F 3/72* (2006.01)
*H03G 1/00* (2006.01)
*H03G 3/00* (2006.01)
*H03G 5/28* (2006.01)

(52) U.S. Cl.
CPC .. *H03F 2200/267* (2013.01); *H03F 2200/408* (2013.01); *H03F 2200/462* (2013.01); *H03F 2203/45156* (2013.01); *H03F 2203/45288* (2013.01); *H03F 2203/45528* (2013.01); *H03F 2203/45701* (2013.01); *H03F 2203/7215* (2013.01); *H03F 2203/7221* (2013.01)

(56) References Cited

U.S. PATENT DOCUMENTS

| | | | | |
|---|---|---|---|---|
| 8,143,946 | B2* | 3/2012 | Aram | H03F 1/26 330/253 |
| 8,200,325 | B2* | 6/2012 | Sarpeshkar | H03F 1/0266 330/261 |
| 8,704,597 | B2* | 4/2014 | Yu | H03F 3/45188 330/253 |
| 8,922,274 | B2* | 12/2014 | Yoon | A61B 5/6846 327/124 |
| 2014/0330102 | A1* | 11/2014 | Zbrzeski | A61B 5/04001 600/377 |
| 2016/0072442 | A1* | 3/2016 | Testi | H03F 3/193 330/278 |

OTHER PUBLICATIONS

Iawei Xu, Refet Firat Yazicioglu, Bernard Grundlehner, Pieter Harpe, Kofi A. A. Makinwa, Fellow and Chris Van Hoof. A 160 µW 8-Channel Active Electrode System for EEG Monitoring, IEEE Transactions on Biomedical Circuits and Systems, Dec. 2011, pp. 555-567, vol. 5, No. 6,IEEE.

Jerald Yoo,Longyan, Dina El-Damak , Muhammad Awais Bin Altaf,Ali H. Shoeb, and Anantha P. Chandrakasan, An 8-Channel Scalable EEG Acquisition SoC With Patient-Specific Seizure Classification and Recording Processor, IEEE Journal of Solid-State Circuits,Jan. 2013, pp. 214-228. vol. 48, No. 1,IEEE.

Chung-Yu Wu,Wei-Mingchen and Liang-Ting Kuo,A CMOS Power-Efficient Low-Noise Current-Mode Front-End Amplifier for Neural Signal Recording, IEEE Transactions on Biomedical Circuits and Systems, Apr. 2013,pp. 107-114, vol. 7, No. 2, IEEE.

* cited by examiner

FRONT-END AMPLIFIER CIRCUITS FOR BIOMEDICAL ELECTRONICS

CROSS REFERENCE TO RELATED APPLICATIONS

This Application claims priority of China Patent Application No. 201610150167.5, filed on Mar. 16, 2016, the entirety of which is incorporated by reference herein.

BACKGROUND OF THE INVENTION

Field of the Invention

The disclosure relates generally to a front-end amplifier circuit for biomedical electronics, and more particularly it relates to a current-mode front-end amplifier circuit for biomedical electronics.

Description of the Related Art

For detecting a biological signal, front-end amplifier circuits plays a significant role in the field of biomedical electronics. Since the characteristics of biological signals include low frequencies and low amplitudes, a proper front-end circuit for amplifying a biological signal should have the characteristic of low noise and high gain. In addition, power consumption should be as low as possible for long-term measurements by a wearable device.

BRIEF SUMMARY OF THE INVENTION

In an embodiment, a front-end amplifier circuit for receiving a biological signal comprises a signal channel. The signal channel amplifies the biological signal to generate a detection current. The signal channel comprises a capacitive-coupled transconductance amplifier. The capacitive-coupled transconductance amplifier amplifies the biological signal with a transconductance gain to generate a first current.

According to an embodiment of the invention, the capacitive-coupled transconductance amplifier comprises a first input capacitor, a second input capacitor, a first common-mode P-type transistor, a second common-mode P-type transistor, a first current source, a second current source, a first transconductance P-type transistor, a second transconductance P-type transistor, a linear resistor, a third transconductance P-type transistor, a fourth transconductance P-type transistor, a first transconductance N-type transistor, a second transconductance N-type transistor, a third transconductance N-type transistor, and a fourth transconductance N-type transistor. The first input capacitor is coupled between a negative input node and a first node. The second input capacitor is coupled between a positive input node and a second node, wherein the first input capacitor and the second input capacitor receive the biological signal by a way of AC-couple in a differential mode. The first common-mode P-type transistor is configured to provide a common-mode voltage for the first node. The second common-mode P-type transistor is configured to provide the common-mode voltage for the second node. The first current source is configured to provide a first transconductance bias current. The second current source is configured to provide a second transconductance bias current. A source terminal of the first transconductance P-type transistor receives the first transconductance bias current, and a gate terminal of the first transconductance P-type transistor is coupled to the second node. A source terminal of the second transconductance P-type transistor receives the second transconductance bias current, and a gate terminal of the second transconductance P-type transistor is coupled to the first node. The first transconductance P-type transistor and the second transconductance P-type transistor are configured to the transconductance gain. The linear resistor is coupled between the source terminal of the first transconductance P-type transistor and the source terminal of the second transconductance P-type transistor, and the linear resistor is configured to improve the linearity of the transconductance gain. A source terminal of the third transconductance P-type transistor is coupled to a drain terminal of the first transconductance P-type transistor, and a gate terminal of the third transconductance P-type transistor receives a transconductance bias voltage. A source terminal of the fourth transconductance P-type transistor is coupled to a drain terminal of the second transconductance P-type transistor, a gate terminal of the fourth transconductance P-type transistor receives the transconductance bias voltage, and a drain terminal of the fourth transconductance P-type transistor is coupled to a transconductance output node. The transconductance output node outputs the first current. A drain terminal and a gate terminal of a first transconductance N-type transistor are both coupled to a drain terminal of the third transconductance P-type transistor. A drain terminal of a second transconductance N-type transistor is coupled to the transconductance output node, and a gate terminal of a second transconductance N-type transistor is coupled to the gate terminal of the first transconductance N-type transistor. A drain terminal and a gate terminal of a third transconductance N-type transistor are both coupled to a source terminal of the first transconductance N-type transistor, and a source terminal of a third transconductance N-type transistor is coupled to a ground. A drain terminal of a fourth transconductance N-type transistor is coupled to a source terminal of the second transconductance N-type transistor, a gate terminal of a fourth transconductance N-type transistor is coupled to the gate terminal of the third transconductance N-type transistor, and a source terminal of a fourth transconductance N-type transistor is coupled to the ground.

According to an embodiment of the invention, the front-end amplifier circuit further comprises a transimpedance amplifier which is configured to amplify the detection current with a transimpedance gain to generate a voltage signal and to provide a driving capability for a coupled measurement system. An amplified ratio of the biological signal converted into the voltage signal is a product of the transconductance gain, the first current gain, and the second current gain.

According to an embodiment of the invention, the bandwidth comprises a low-pass cut-off frequency and a high-pass cut-off frequency, wherein the transconductance and the low-pass capacitor determine the low-pass cut-off frequency, wherein the first coupling capacitor and the channel resistance determine the high-pass cut-off frequency.

According to an embodiment of the invention, the first bias P-type transistor is operated in a cut-off region, such that the channel resistance is at a high resistance level.

According to an embodiment of the invention, the offset cancellation circuit comprises a digital controller, a pseudo resistor reset module, an offset detector, a first current digital-to-analog converter, a second current digital-to-analog converter, a third current digital-to-analog converter, and a register. The digital controller generates a first reset signal, a second reset signal, and a selection signal. The pseudo resistor reset module shorts the first node and the second node to the common-mode voltage according to the first reset signal, and shorts the first positive input node to the common-mode voltage and the third positive input node to the DC bias voltage according to the second reset signal. The offset detector sequentially detects the first current, the second current, and the detection current according to the selection signal to generate a first compensation code, a second compensation code, and a third compensation code. The first current digital-to-analog converter sinks or sources a first compensation current to the transconductance output node according to the first compensation code. The second current digital-to-analog converter sinks or sources a second compensation current to the band-pass output node according to the second compensation code. The third current digital-to-analog converter sinks or sources a third compensation current to the programmable-gain output node according to the third compensation code. The register is configured to store the first compensation code, the second compensation code, and the third compensation code.

According to an embodiment of the invention, the offset cancellation circuit further comprises a first switch and a second switch. The first switch is coupled between the capacitive-coupled transconductance amplifier and the band-pass filtering amplifier and turned OFF by the digital controller. The second switch is coupled between the band-pass filtering amplifier and the programmable-gain amplifier and turned OFF by the digital controller.

According to an embodiment of the invention, when the first switch and the second switch are both turned OFF, the offset detector, according to the selection signal, detects the first current to generate the first compensation code. When the first switch is turned ON and the second switch is turned OFF, the first current digital-to-analog converter sinks or sources the first compensation current to the transconductance output node, and the offset detector, according to the selection signal, detects the second current to generate the second compensation code. When the first switch and the second switch are both turned ON, the first current digital-to-analog converter sinks or sources the first compensation current to the transconductance output node, the second current digital-to-analog converter sinks or sources the second compensation current to the band-pass output node, and the offset detector, according to the selection signal, detects the detection current to generate the third compensation code.

According to an embodiment of the invention, the offset detector further comprises a signal converter, a selector, and a comparator. The signal converter converts an input current into an offset voltage. The selector sequentially selects one of the first current, the second current, and the detection current to be the input current according to the selection signal. The comparator compares the offset voltage with the common-mode voltage to generate a digital compensation signal. The digital controller determines the first compensation code, the second compensation code, and the third compensation code according to the digital compensation signal.

According to an embodiment of the invention, the front-end amplifier circuit further comprises another signal channel and a multiplexer. Another signal channel receives and amplifies another biological signal to generate another detection current. The multiplexer provides one of the detection current and the other detection current for the transimpedance amplifier.

A detailed description is given in the following embodiments with reference to the accompanying drawings.

BRIEF DESCRIPTION OF DRAWINGS

The invention can be more fully understood by reading the subsequent detailed description and examples with references made to the accompanying drawings, wherein.

DETAILED DESCRIPTION OF THE INVENTION

Figure 1:
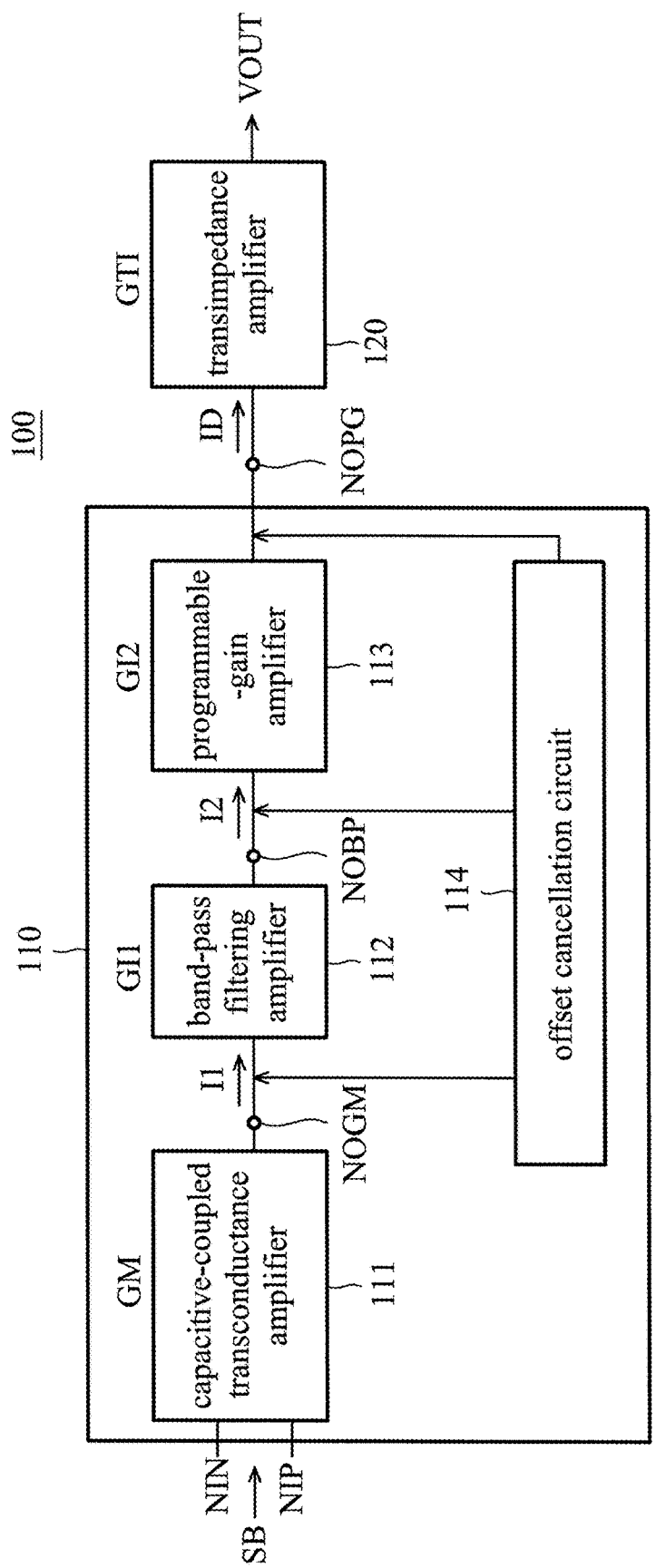
FIG. 1 is a block diagram of a front-end amplifier circuit in accordance with an embodiment of the invention.

This description is made for the purpose of illustrating the general principles of the invention and should not be taken in a limiting sense. In addition, the present disclosure may repeat reference numerals and/or letters in the various examples. This repetition is for the purpose of simplicity and clarity and does not in itself dictate a relationship between the various embodiments and/or configurations discussed. The scope of the invention is best determined by reference to the appended claims.

It should be understood that the following disclosure provides many different embodiments, or examples, for implementing different features of the application. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a feature on, connected to, and/or coupled to another feature in the present disclosure that follows may include embodiments in which the features are formed in direct contact, and may also include embodiments in which additional features may be formed interposing the features, such that the features may not be in direct contact.

FIG. 1 is a block diagram of a front-end amplifier circuit in accordance with an embodiment of the invention. As shown in FIG. 1, the front-end amplifier circuit 100 is configured to amplify the biological signal SB received through the positive node NIP and the negative node NIN to generate the amplified voltage signal VOUT. After a digital-to-analog converter converts the voltage signal VOUT into digital data, the physical condition could be immediately informed by digital signal processing for real-time monitoring or treatment.

According to an embodiment of the invention, the biological signal SB is an Electroencephalography (EEG) signal. According to another embodiment of the invention, the biological signal SB is an Electrocorticography (ECoG) signal. According to yet another embodiment of the invention, the biological signal SB is a local field potential (LFP) signal. According to yet another embodiment of the invention, the biological signal SB is an Electrocardiography (ECG) signal. According to yet another embodiment of the invention, the biological signal SB is an Electromyography (EMG) signal. According to other embodiments of the invention, the biological signal SB may be any other known or Unknown type of biological signal.

The front-end amplifier circuit 100 includes a signal channel 110 and a transimpedance amplifier 120. The signal channel 110 amplifies the biological signal SB received through the input positive node NIP and the input negative node NIN to generate the detection current ID. The transimpedance amplifier 120 amplifies the detection current ID with the transimpedance gain GTI to generate the voltage signal VOUT.

The signal channel 110 includes a capacitive-coupled transconductance amplifier 111, a band-pass filtering amplifier 112, a programmable-gain amplifier 113, and an offset cancellation circuit 114, in which the capacitive-coupled transconductance amplifier 111 amplifies the biological signal SB with the transconductance gain GM to generate the first current I1 on the transconductance output node NOGM. The band-pass filtering amplifier 112 filters the noise in the first current I1 outside the bandwidth BW and amplifies the first current I1 with the first current gain GI1 to generate the second current I2 on the band-pass output node NOBP.

The programmable-gain amplifier 113 amplifies the second current I2 with the second current gain GI2 to generate the detection current ID on the programmable-gain output node NOPG, in which the second current gain GI2 may be programmed. The offset cancellation circuit 114 is configured to cancel the output offset currents of the capacitive-coupled transconductance amplifier 111, the band-pass filtering amplifier 112, and the programmable-gain amplifier 113, and the detailed actions will be described in the following paragraphs.

Figure 2:
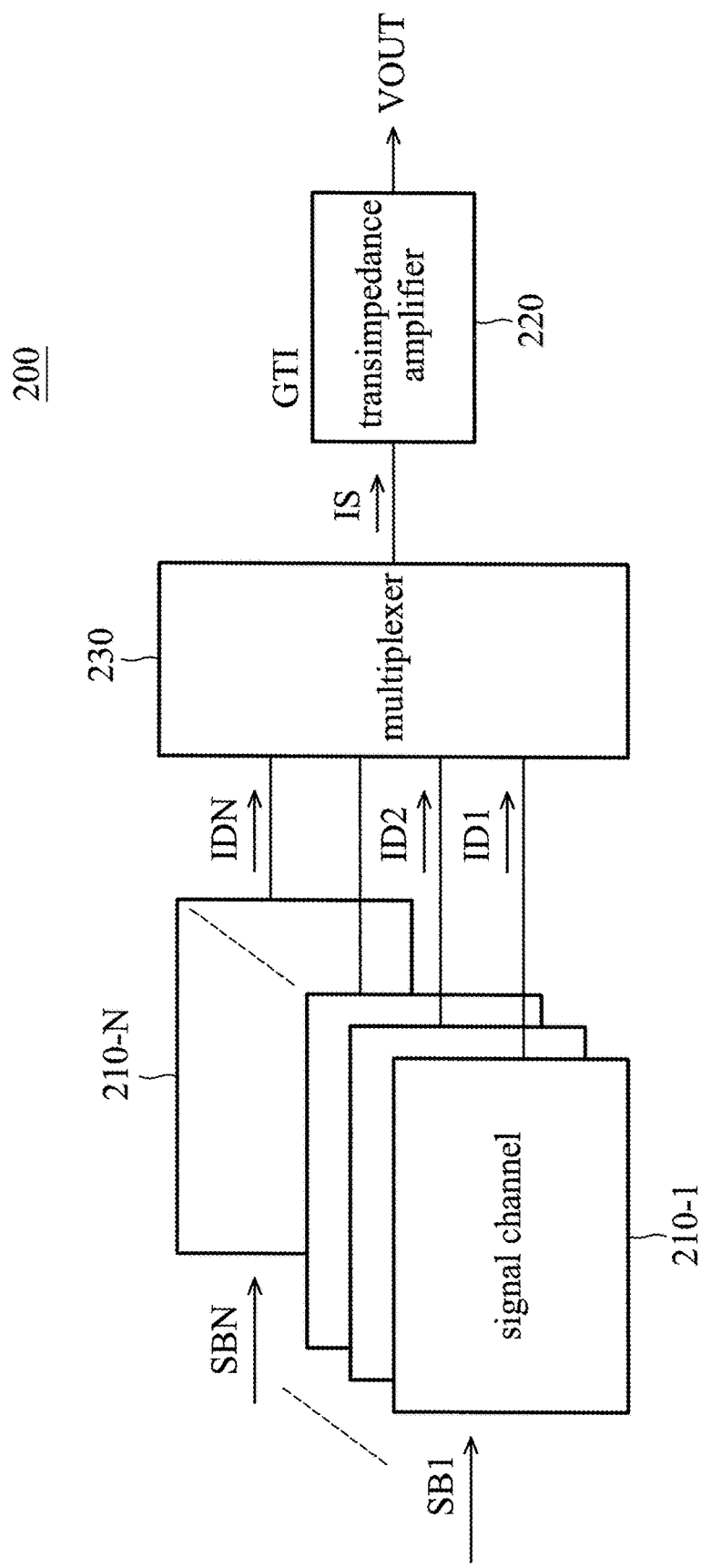
FIG. 2 is a block diagram of a front-end amplifier circuit in accordance with another embodiment of the invention.

FIG. 2 is a block diagram of a front-end amplifier circuit in accordance with another embodiment of the invention. As shown in FIG. 2, the front-end amplifier circuit 200 includes a plurality of signal channels 210_1~210_N, a transimpedance amplifier 220, and a multiplexer 230. The signal channels 210_1~210_N respectively receive a plurality of biological signal SB1~SBN to generate a plurality of detection currents ID1~IDN. The multiplexer 230 selects one of the detection currents ID1~IDN to be the selected current IS. The transimpedance amplifier 220 amplifies the selected current IS with the transimpedance gain GTI to generate the voltage signal VOUT.

According to an embodiment of the invention, a plurality of signal channels 210_1~210_N are the same as the signal channel 110 in FIG. 1. According to another embodiment of the invention, a part of the signal channels 210_1~210_N may be the same as the signal channel 110 in FIG. 1, and a part of the signal channels 210~210_N may be different from the signal channel 110 in FIG. 1.

Figure 3:
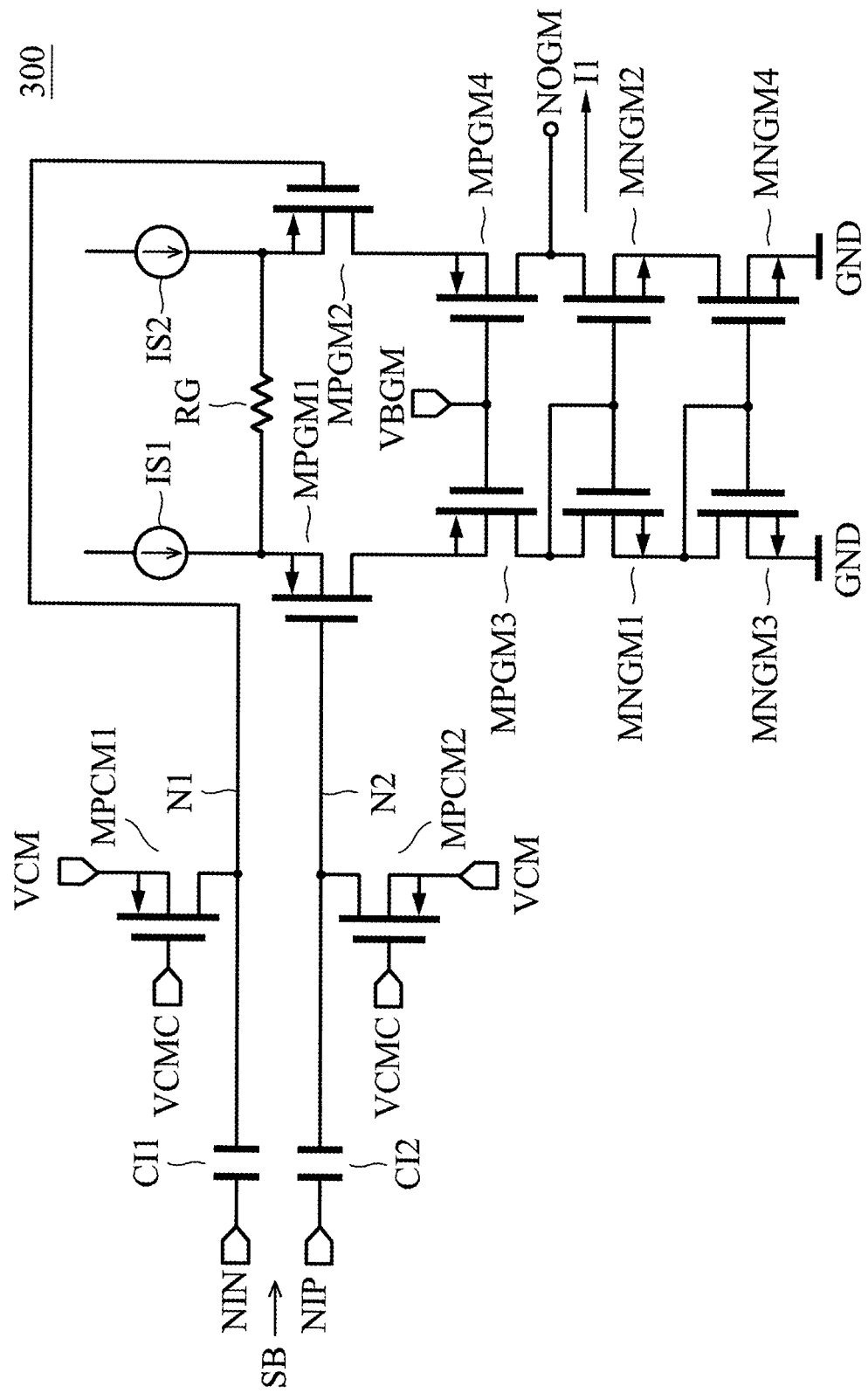
FIG. 3 is a schematic diagram of a capacitive-coupled transconductance amplifier in accordance with an embodiment of the invention.

FIG. 3 is a schematic diagram of a capacitive-coupled transconductance amplifier in accordance with an embodiment of the invention. As shown in FIG. 3, the capacitive-coupled transconductance amplifier 300 includes a first input capacitor CI1, the second input capacitor CI2, the first common-mode P-type transistor MPCM1, the second common-mode P-type transistor MPCM2, the first current source IS1, the second current source IS2, the first transconductance P-type transistor MPGM1, the second transconductance P-type transistor MPGM2, the linear resistor RG, the third transconductance P-type transistor MPGM3, the fourth transconductance P-type transistor MPGM4, the first transconductance N-type transistor MNGM1, the second transconductance N-type transistor MNGM2, the third transconductance N-type transistor MNGM3, and the fourth transconductance N-type transistor MNGM4.

The first input capacitor CI1 is coupled between the input negative node NIN and the first node N1, and the second input capacitor CI2 is coupled between the input positive node NIP and the second node N2, in which the first input capacitor CI1 and the second input capacitor CI2 receive the biological signal SB by a way of AC-couple in a differential mode. The first common-mode P-type transistor MPCM1 is configured to apply the common-mode voltage VCM to the first node N1 according to the common-mode control voltage VCMC. The second common-mode P-type transistor MPCM2 is configured to apply the common-mode voltage VCM to the second node N2 according to the common-mode control voltage VCMC.

According to an embodiment of the invention, the first common-mode P-type transistor MPCM1 and the second common-mode P-type transistor MPCM2 are both operated in the cut-off region to generate the channel resistance at the high resistance level. According to another embodiment of the invention, the first common-mode P-type transistor MPCM1 and the second common-mode P-type transistor MPCM2 may be both operated in the triode region.

The source terminal of the first transconductance P-type transistor MPGM1 receives the first transconductance bias current provided by the first current source IS1, and the gate terminal of the first transconductance P-type transistor MPGM1 is coupled to the second node N2. The source terminal of the second transconductance P-type transistor MPGM2 receives the second transconductance bias current of the second current source IS2, and the gate terminal of the second transconductance P-type transistor MPGM2 is coupled to the first node N1. The first transconductance P-type transistor MPGM1 and the second transconductance P-type transistor MPGM2 are configured to generate the transconductance gain GM. The linear resistor RG is coupled between the source terminal of the first transconductance P-type transistor MPGM1 and the source terminal of the second transconductance P-type transistor MPGM2, which is configured to improve the linearity of the transconductance gain GM.

The source terminal of the third transconductance P-type transistor MPGM3 is coupled to the drain terminal of the first transconductance P-type transistor MPGM1, and the gate terminal of the third transconductance P-type transistor MPGM3 is supplied by the transconductance bias voltage VBGM. The source terminal of the fourth transconductance P-type transistor MPGM4 is coupled to the drain terminal of the second transconductance P-type transistor MPGM2. The gate terminal of the fourth transconductance P-type transistor MPGM4 is supplied by the transconductance bias voltage VBGM. The drain terminal of the fourth transconductance P-type transistor MPGM4 is coupled to the transconductance output node NOGM, in which the transconductance output node NOGM outputs the first current I1.

The drain terminal and the gate terminal of the first transconductance N-type transistor MNGM1 are both coupled to the drain terminal of the third transconductance P-type transistor MPGM3. The drain terminal of the second transconductance N-type transistor MNGM2 is coupled to the transconductance output node NOGM, and the gate terminal of the second transconductance N-type transistor MNGM2 is coupled to the gate terminal of the first transconductance N-type transistor MNGM1.

The drain terminal and the gate terminal of the third transconductance N-type transistor MNGM3 are both coupled to the source terminal of the first transconductance N-type transistor MNGM1, and the source terminal of the third transconductance N-type transistor MNGM3 is coupled to the ground GND. The drain terminal of the fourth transconductance N-type transistor MNGM4 is coupled to the source terminal of the second transconductance N-type transistor MNGM2, the gate terminal of the fourth transconductance N-type transistor MNGM4 is coupled to the gate terminal of the third transconductance N-type transistor MNGM3, and the source terminal of the fourth transconductance N-type transistor MNGM4 is coupled to the ground GND.

Figure 4:
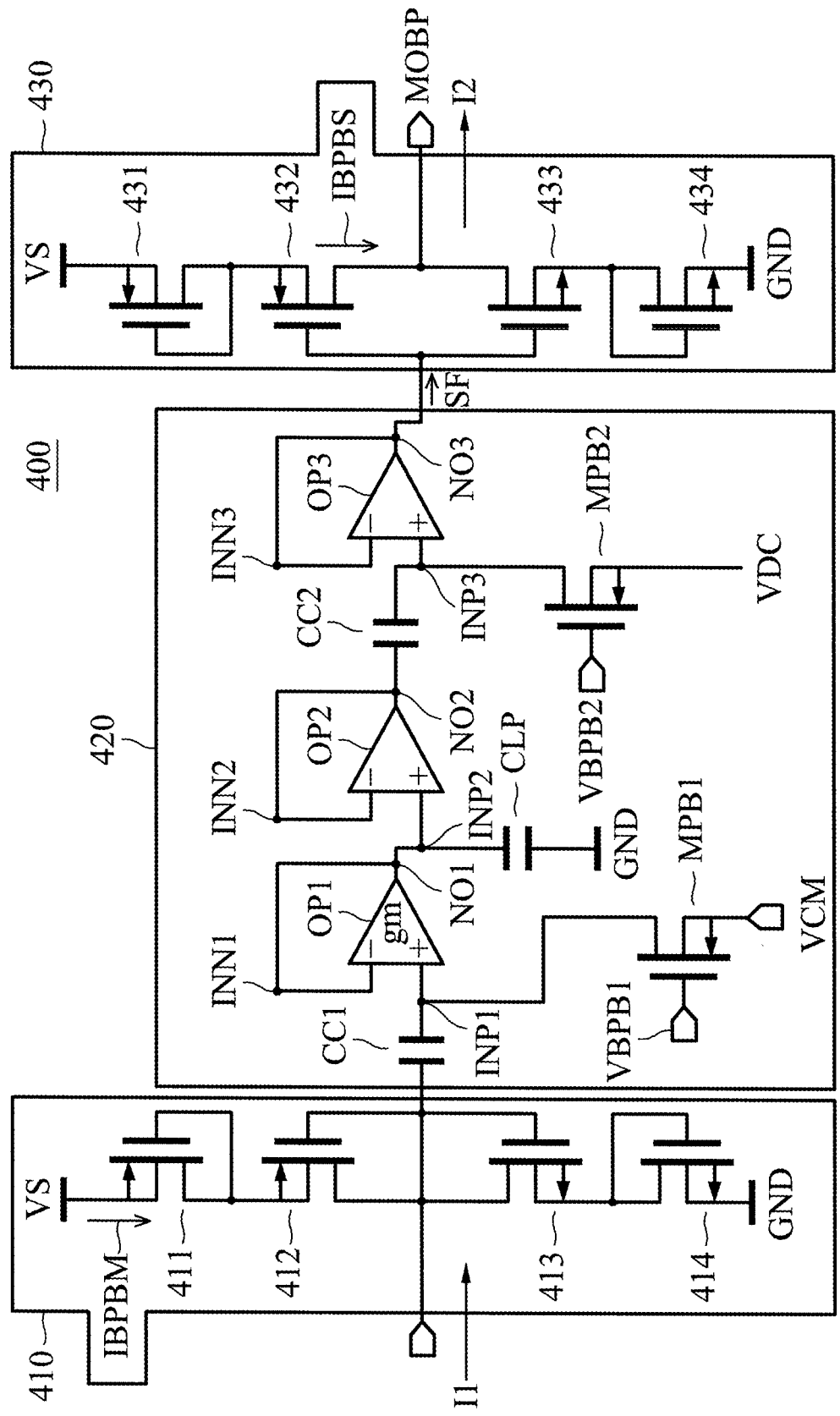
FIG. 4 is a schematic diagram of a band-pass filter in accordance with an embodiment of the invention.

FIG. 4 is a schematic diagram of a band-pass filter in accordance with an embodiment of the invention. As shown in FIG. 4, band-pass filtering amplifier 400 includes the master band-pass current path 410, the band-pass filter 420, and the slave band-pass current path 430. The master band-pass current path 410 flows the master band-pass bias current IBPBM, which is configured to receive the first current I1. The slave band-pass current path 430 flows the slave band-pass bias current IBPBS, which generates the second current I2 according to the filter signal SF. The first current gain GI1 is the ratio of the slave band-pass bias current IBPBS to the master band-pass bias current IBPBM.

The band-pass filter 420 is AC-coupled to the master band-pass current path 410, which is configured to filter the noise in the first current I1 outside the bandwidth BW to provide the filter signal SF for the slave band-pass current path 430. The functions of the master band-pass current path 410, the band-pass filter 420, and the slave band-pass current path 430 will be described in detail in the following paragraphs.

According to an embodiment of the invention, the master band-pass current path 410 includes the first master P-type transistor 411, the second master P-type transistor 412, the first master N-type transistor 413, and the second master N-type transistor 414. The source terminal of the first master P-type transistor 411 is supplied by the supply voltage VS, the gate terminal and the drain terminal of the first master P-type transistor 411 are coupled together. The source terminal of the second master P-type transistor 412 is coupled to the drain terminal of the first master P-type transistor 411, and the gate terminal and the drain terminal of the second master P-type transistor 412 receive the first current I1 of the capacitive-coupled transconductance amplifier 111 in FIG. 1 and of the capacitive-coupled transconductance amplifier 300 in FIG. 3.

The gate terminal and the drain terminal of the first master N-type transistor 413 are coupled to the drain terminal and the gate terminal of the second master P-type transistor 412. The gate terminal and the drain terminal of the second master N-type transistor 414 are coupled to the source terminal of the first master N-type transistor 413, and the source terminal of the second master N-type transistor 414 is coupled to the ground GND.

According to an embodiment of the invention, the first master P-type transistor 411, the second master P-type transistor 412, the first master N-type transistor 413, and the second master N-type transistor 414 are all operated in the sub-threshold region for reducing power consumption. According to another embodiment of the invention, the master band-pass current path 410 may be formed by the second master P-type transistor 412 and the first master N-type transistor 413, such that the gate-to-source voltages of the second master P-type transistor 412 and the first master N-type transistor 413 are increased to raise the master band-pass bias current IBPBM, resulting in increased power consumption.

Similarly, the slave band-pass current path 430 includes the first slave P-type transistor 431, the second slave P-type transistor 432, the first slave N-type transistor 433, and the second slave N-type transistor 434. The source terminal of the first slave P-type transistor 431 is coupled to the supply voltage VS, the gate terminal and the drain terminal of the first slave P-type transistor 431 are coupled together. The source terminal of the second slave P-type transistor 432 is coupled to the drain terminal of the first slave P-type transistor 431, and the drain terminal of the second P-type transistor 432 is coupled to the band-pass output node NOBP.

The gate terminal of the first slave N-type transistor 433 is coupled to the gate terminal of the second slave P-type transistor 432, the drain terminal of the first slave N-type transistor 433 is coupled to the band-pass output node NOBP to output the second current I2, and the gate terminal of the first slave N-type transistor 433 receives the filter signal SF. The gate terminal and the drain terminal of the second N-type transistor 434 are coupled to the source terminal of the first slave N-type transistor 433, and the source terminal of the second N-type transistor 434 is coupled to the ground GND.

According to an embodiment of the invention, the first slave P-type transistor 431, the second slave P-type transistor 432, the first slave N-type transistor 433, and the second slave N-type transistor 434 are all operated in the sub-threshold region to reduce power consumption. According to another embodiment of the invention, the slave band-pass current path 430 is the same as the master band-pass current path 410 so that the slave band-pass current path 430 may also be formed by the second slave P-type transistor 432 and the first slave N-type transistor 433. However, the gate-to-source voltages of the second slave P-type transistor 432 and the first slave N-type transistor 433 are increased to raise the slave band-pass bias current IBPBS, resulting in increased power consumption.

According to an embodiment of the invention, the ratio of the transistor sizes in the slave band-pass current path 430 to those in the master band-pass current path 410 is the ratio of the slave band-pass bias current IBPBS to the master band-pass bias current IBPBM, and is the first current gain GI1 as well.

According to an embodiment of the invention, the band-pass filter 420 includes a first differential-input amplifier OP1, a first coupling capacitor CC1, a first bias P-type transistor MPB1, a low-pass capacitor CLP, a second differential-input amplifier OP2, a third differential-input amplifier OP3, a second coupling capacitor CC2, and a second bias P-type transistor MPB2.

The first differential-input amplifier OP1 is configured to generate the transconductance gm, and includes a first negative input node INN1, a first positive input node INP1, and a first output node NO1, in which the first negative input node INN1 is coupled to the first output node NO1. The first coupling capacitor CC1 is coupled between the gate terminal of the second master P-type transistor 412 and the first positive input node INP1. The first bias P-type transistor MPB1 has channel resistance, in which the source terminal of the first bias P-type transistor MPB1 is coupled to the common-mode voltage VCM, the drain terminal of the first bias P-type transistor MPB1 is coupled to the first positive input node INP1, and the gate terminal of the first bias P-type transistor MPB1 is coupled to the first band-pass bias voltage VBPB1.

The low-pass capacitor CLP is coupled between the first output node NO1 and the ground GND. The second differential-input amplifier OP2 includes a second negative input node INN2, a second positive input node INP2, and a second output node NO2, in which the second negative input node INN2 is coupled to the second output node NO2 and the second positive input node INP2 is coupled to the first output node NO1. The third differential-input amplifier OP3 includes a third negative input node INN3, a third positive input node INP3, and a third output node NO3, in which the third negative input node INN3 is coupled to the third output node NO3 which outputs the filter signal SF.

The second coupling capacitor CC2 is coupled between the second output node NO2 and the third positive input node INP3 to isolate the second differential-input amplifier OP2 from the third differential-input amplifier OP3. The second bias P-type transistor MPB2 is configured to provide the DC bias voltage VDC for the third positive input node INP3 according to the second band-pass bias voltage VBPB2, such that the bias voltage of the gate terminal of the second slave P-type transistor 432 and the gate terminal of the first slave N-type transistor 433 is the same as that of the gate terminal of the second master P-type transistor 412 and the gate terminal of the first master N-type transistor 413.

Figure 5:
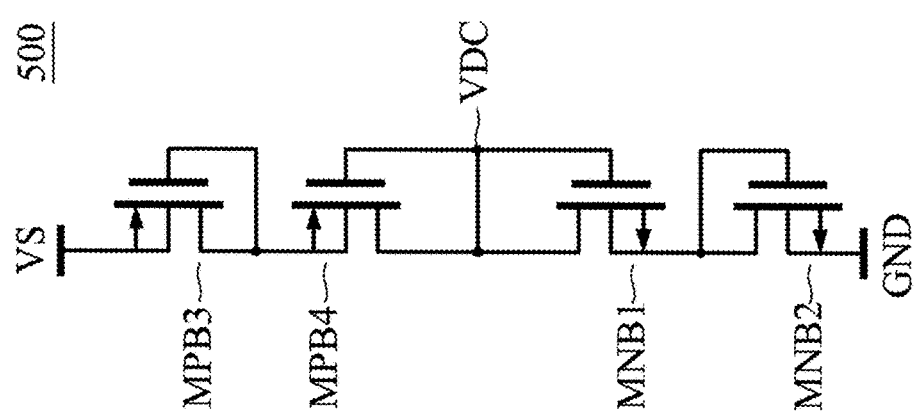
FIG. 5 is a schematic diagram of a DC-bias generator in accordance with an embodiment of the invention.

FIG. 5 is a schematic diagram of a DC-bias generator in accordance with an embodiment of the invention. As shown in FIG. 5, the DC bias generator 500 includes the third bias P-type transistor MPB3, the fourth bias P-type transistor MPB4, the first N-type transistor MNB1, and the second bias N-type transistor MNB2.

According to an embodiment of the invention, the sizes of the third bias P-type transistor MPB3, the fourth bias P-type transistor MPB4, the first bias N-type transistor MNB1, and the second bias N-type transistor MNB2 are equal to the respective sizes of the first master P-type transistor 411, the second master P-type transistor 412, the first master N-type transistor 413, and the fourth master N-type transistor 414, only reduced by a predetermined ratio. Therefore, the generated DC bias voltage VDC is very close to the voltage of the gate terminal of the second master P-type transistor 412.

Referring to FIG. 4, according to an embodiment of the invention, the first bias P-type transistor MPB1 and the second bias P-type transistor MPB2 are operated in the cut-off region, such that its channel resistance is at the high resistance level. According to an embodiment of the invention, the bandwidth BW of the band-pass filter 420 includes a low-pass cut-off frequency and a high-pass cut-off frequency, in which the transconductance gm generated by the first differential-input amplifier OP1 and the low-pass capacitor CLP are configured to determine the low-pass cut-off frequency, and the first coupling capacitor CC1 and the channel resistance of the first bias P-type transistor MPB1 are configured to determine the high-pass cut-off frequency.

Figure 6:
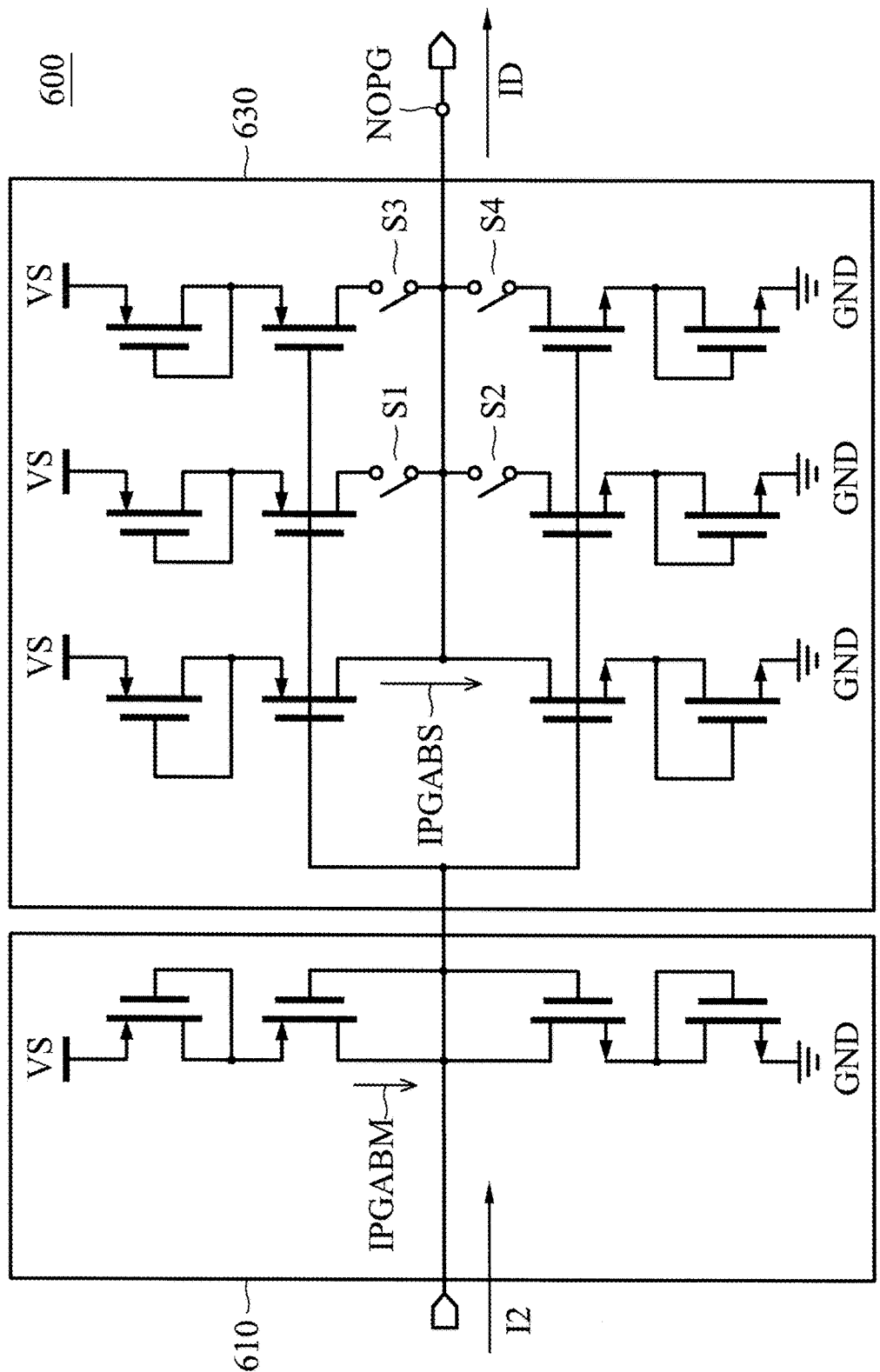
FIG. 6 is a schematic diagram of a programmable-gain amplifier in accordance with an embodiment of the invention.

FIG. 6 is a schematic diagram of a programmable-gain amplifier in accordance with an embodiment of the invention. The programmable-gain amplifier 600 includes a master programmable-gain current path 610 and a slave programmable-gain current path 630, which is configured to amplify the second current I2 to generate detection current ID on the programmable-gain output node NOPG.

As shown in FIG. 6, the master programmable-gain current path 610 is similar to the master band-pass current path 410, and the slave programmable-gain current path 630 is similar to the slave band-pass current path 430. Therefore, the operating principle of the master programmable-gain current path 610 and the slave programmable-gain current path 630 is the same as that of the master band-pass current path 410 and the slave band-pass current path 430, which is discussed no more herein.

Since the slave programmable-gain bias current IPGABS of the slave programmable-gain current path 630 can be raised by the first adjustment switch S1, the second adjustment switch S2, the third adjustment switch S3, and the fourth adjustment switch S4, the ratio of the slave programmable-gain bias current IPGABS to the master programmable-gain bias current IPGABM can be increased or decreased for adjusting the second current gain GI2.

Figure 7:
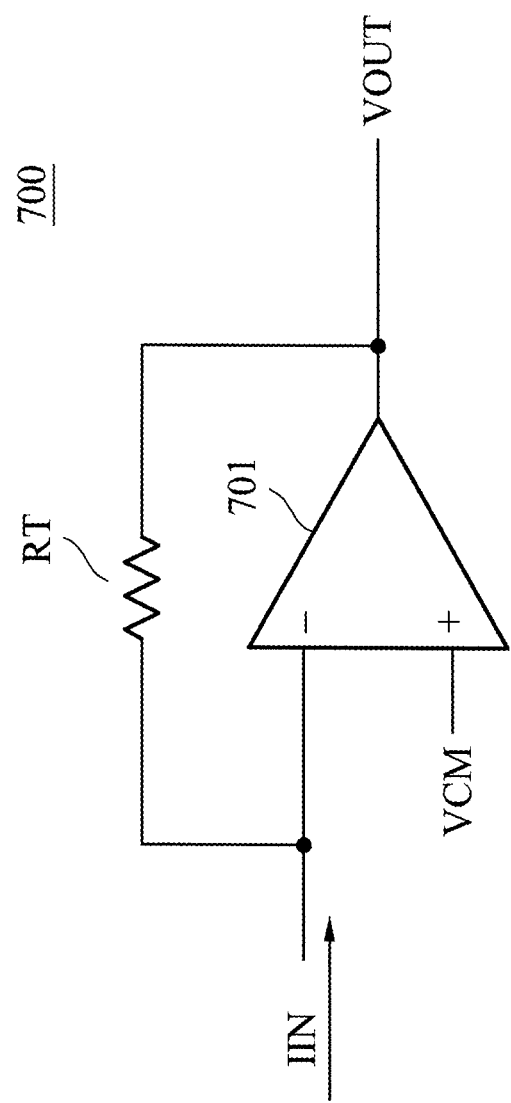
FIG. 7 is a schematic diagram of a transimpedance amplifier in accordance with an embodiment of the invention.

FIG. 7 is a schematic diagram of a transimpedance amplifier in accordance with an embodiment of the invention. As shown in FIG. 7, the transimpedance amplifier 700 includes a fourth differential-input amplifier 701 and a feedback resistor RT, which is configured to convert the input current IIN into the voltage signal VOUT. The fourth differential-input amplifier 701 includes a positive input node, a negative input node, and an output node, and the feedback resistor RT is coupled between the negative input node and the output node of the fourth differential-input amplifier 701.

The positive input node of the fourth differential-input amplifier 701 is supplied by the common-mode voltage VCM, and the negative input node of the fourth differential-input amplifier 701 receives the input current IIN. According to an embodiment of the invention, the input current IIN is the detection current ID shown in FIG. 1 or the selected current IS shown in FIG. 2, and the transimpedance gain GTI is determined by the feedback resistor RT.

Figure 8:
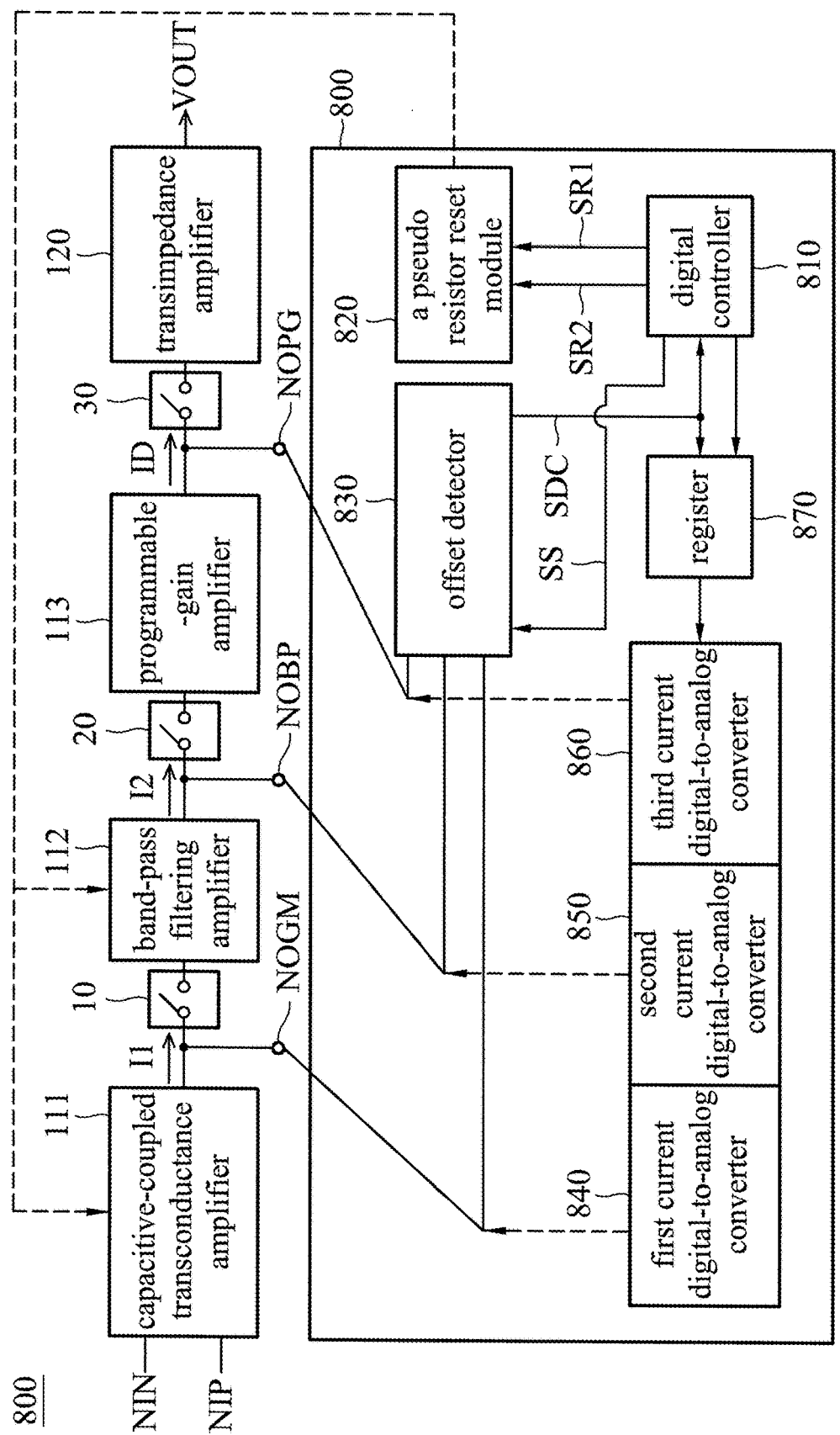
FIG. 8 is a schematic diagram of an offset cancellation circuit in accordance with an embodiment of the invention.

FIG. 8 is a schematic diagram of an offset cancellation circuit in accordance with an embodiment of the invention. As shown in FIG. 8, the offset cancellation circuit 800 includes a digital controller 810, a pseudo resistor reset module 820, an offset detector 830, a first current digital-to-analog converter 840, a second current digital-to-analog converter 850, a third current digital-to-analog converter 860, a first switch 10, a second switch 20, a third switch 30, and a register 870, in which the offset cancellation circuit 800 is an embodiment of the offset cancellation circuit 114 in FIG. 1. According to an embodiment of the invention, the pseudo resistor reset module 820 shorts the first node N1 and the second node N2 in FIG. 3 to the common-mode voltage VCM by pulling the common-mode control voltage VCMC to the ground GND.

The digital controller 810 controls, using the first reset signal SR1, the pseudo resistor reset module 820 to short the first node N1 and the second node N2 in FIG. 3 to the common-mode voltage VCM, in order to determine the output offset current of the capacitive-coupled transconductor 300. In addition, the digital controller 810 controls, using the second reset signal SR2, the pseudo resistor reset module 820 to short the first positive input node INP1 in FIG. 4 to the common-mode voltage VCM and to short the third positive input node INP3 to the DC bias voltage VDC so that the output offset current of the band-pass filtering amplifier 400 can be determined.

According to an embodiment of the invention, the pseudo resistor reset module 820, by pulling the first band-pass bias voltage VBPB1 and the second band-pass bias voltage VPB2 to the ground GND, shorts the first positive input node INP1 to the common-mode voltage VCM and shorts the third positive input node INP3 to the DC bias voltage VDC.

The offset detector 830 sequentially selects one of the first current I1, the second current I2, and the detection current ID to generate the digital compensation signal SDC according to the selection signal SS generated by the digital controller 810. The digital compensation signal SDC includes a first compensation code, a second compensation code, and a third compensation code respectively corresponding to the first current I1, the second current I2, and the detection current ID. The first compensation code, the second compensation code, and the third compensation code are configured to respectively control the first digital-to-analog converter 840, the second digital-to-analog converter 850, and the third digital-to-analog converter 860, and the digital controller 810 stores the digital compensation signal SDC in the register 870.

Figure 9:
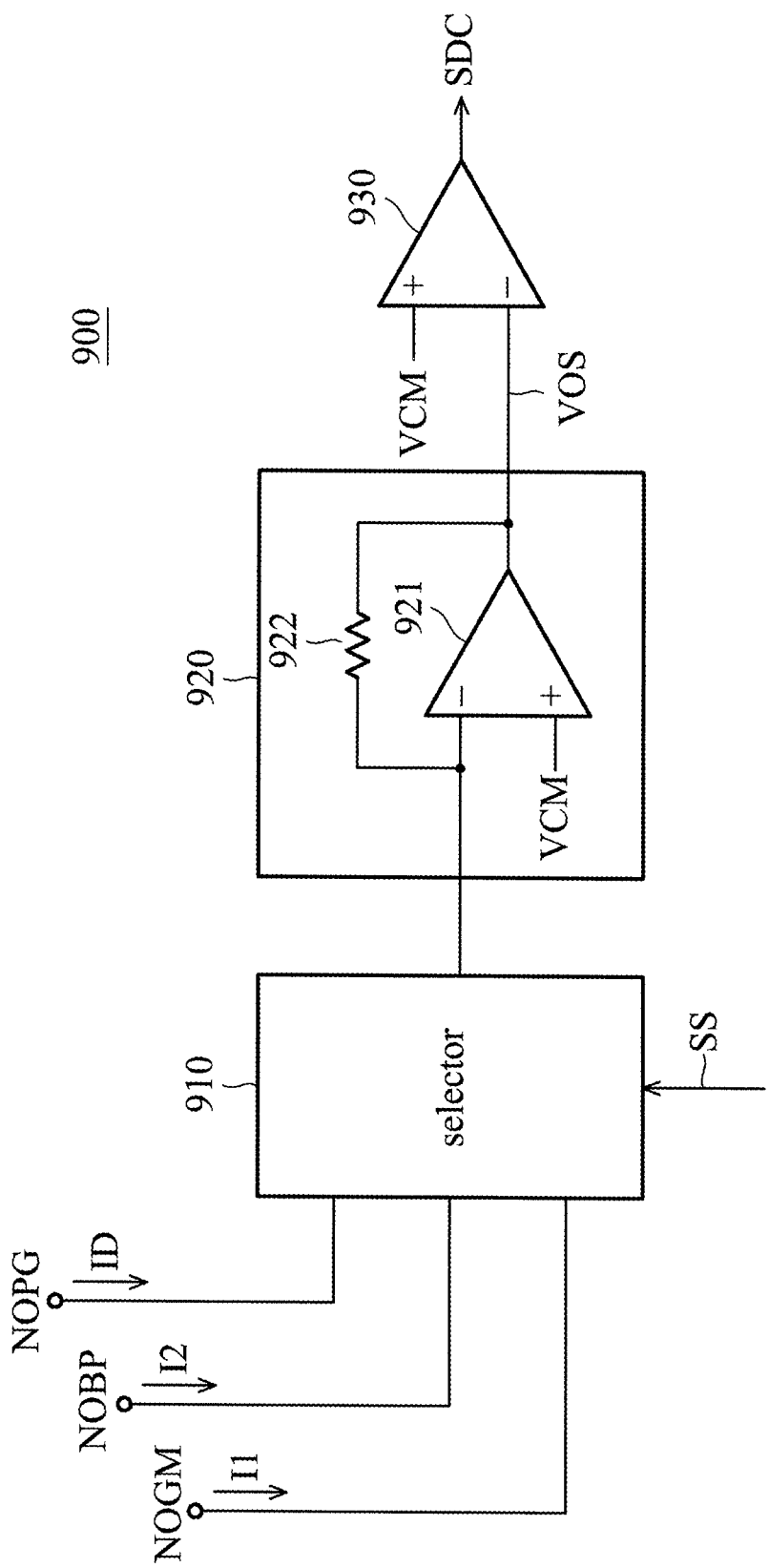
FIG. 9 is a schematic diagram of an offset-detection circuit in FIG. 8 in accordance with an embodiment of the invention.

FIG. 9 is a schematic diagram of an offset-detection circuit in FIG. 8 in accordance with an embodiment of the invention. As shown in FIG. 9, the offset detector 900 includes a selector 910, a signal converter 920, and the comparator 930, which is configured to sequentially select the first current I1, the second current I2, and the detection current ID to generate the first compensation code, the second compensation code, and the third compensation code of the digital compensation signal SDC.

The selector 910 is configured to sequentially provide one of the first current I1, the second current I2, and the detection current ID for the signal converter 920 according to the selection signal SS. The signal converter 920 includes an amplifier 921 and a negative-feedback resistor 922, which is configured to convert one of the first current I1, the second I2, and the detection current ID selected by the selector 910 into the offset voltage VOS. The comparator 930 compares the common-mode voltage VCM with the offset voltage VOS to generate the digital compensation signal SDC.

The digital controller 810 in FIG. 8, according to the sequentially generated digital compensation signal SDC, determines the first compensation code, the second compensation code, and the third compensation code to control the compensation currents provided for the transconductance output node NOGM, the band-pass output node NOBP, and programmable-gain output node NOPG.

Referring to FIG. 8, according to an embodiment of the invention, the digital controller 810 controls the first switch 10, the second switch 20, and the third switch 30 to be turned ON or OFF for individually measuring the output offset currents of the capacitive-coupled transconductance amplifier 111, the band-pass filtering amplifier 112, and the programmable-gain amplifier 113. The detailed actions will be discussed in the following paragraphs. According to another embodiment of the invention, the third switch 30 may be substituted by the multiplexer 230 of the front-end amplifier circuit 200 in FIG. 2.

Figure 10:
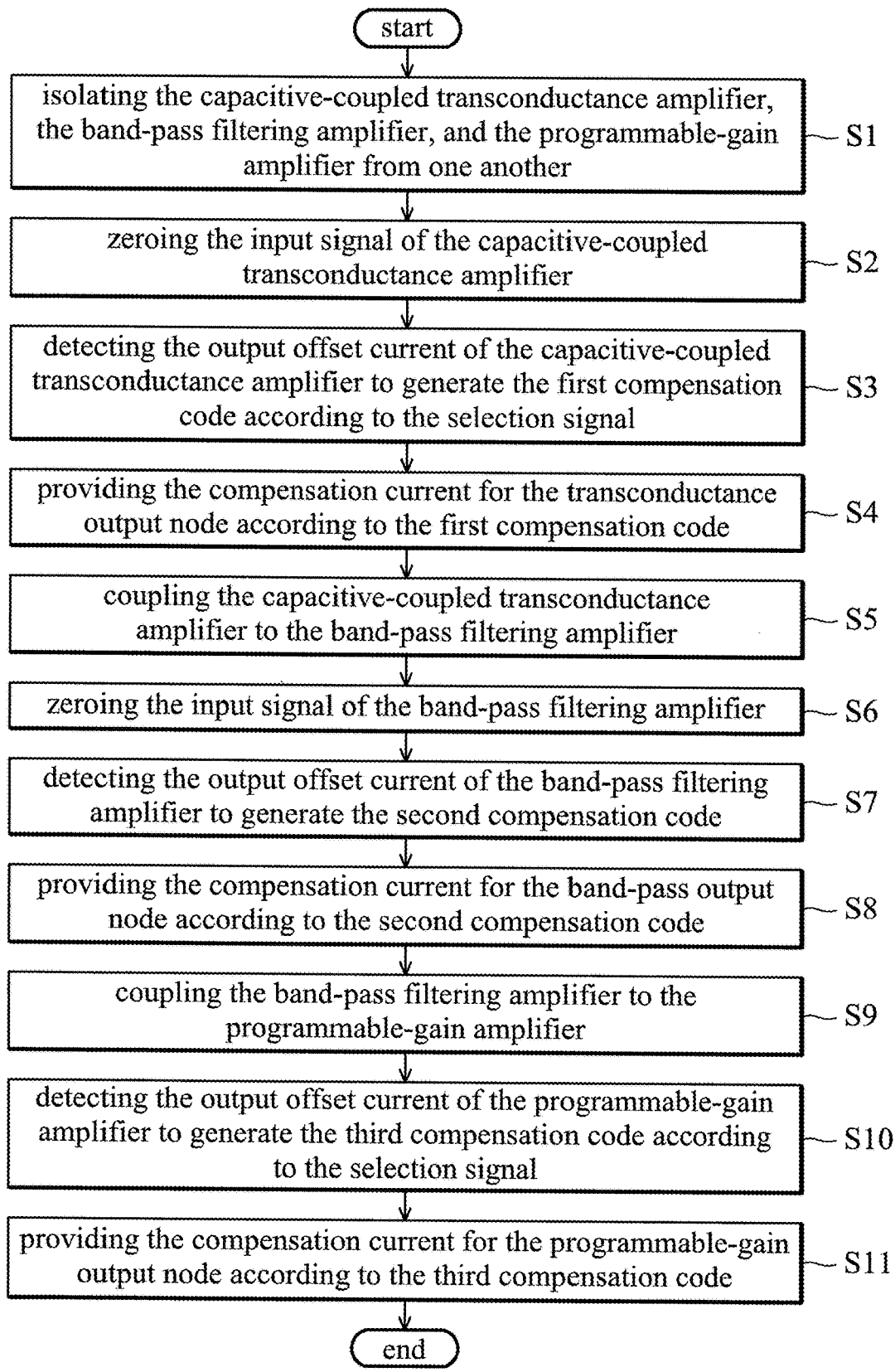
FIG. 10 is a flow chart of an offset-detection method in accordance with an embodiment of the invention.

FIG. 10 is a flow chart of an offset-detection method in accordance with an embodiment of the invention. The flow chart in FIG. 10 will be explained with FIGS. 1, 3, 4, and 8 for a detailed explanation.

First, the first switch 10, the second switch 20, and the third switch 30 in FIG. 8 are turned OFF by the digital controller 810, in order to isolate the capacitive-coupled transconductance amplifier 111, the band-pass filtering amplifier 112, and the programmable-gain amplifier 113 from one another (Step S1). In addition, the pseudo resistor reset module 820 is controlled by the first reset signal SR1 to short the first node N1 and the second node N2 of the capacitive-coupled transconductance amplifier 300 in FIG. 3 to the common-mode voltage VCM, so that the input signal of the capacitive-coupled transconductance amplifier 111 in FIG. 8 is returned to zero for detecting the output offset current of the capacitive-coupled transconductance amplifier 111 (Step S2).

The offset detector 830, according to the selection signal SS, detects the first current I1 to generate the first compensation code of the digital compensation signal SDC and stores the first compensation code in the register 870 (Step S3). The digital controller 810, according to the first compensation code, controls the first current digital-to-analog converter 840 to provide the compensation current for the transconductance output node NOGM (Step S4).

Then, the digital controller 810 turns the first switch 10 ON to couple the capacitive-coupled transconductance amplifier 111 to the band-pass filtering amplifier 112 (Step S5). The digital controller 810, according to the second reset signal SR2, controls the pseudo resistor reset module 820 to short the first positive node INP1 of the band-pass filtering amplifier 400 in FIG. 4 to the common-mode voltage VCM and to short the third positive input node INP3 to the DC bias voltage VDC, so that the input signal of the band-pass filtering amplifier 112 in FIG. 8 is returned to zero for detecting the output offset current of the band-pass filtering amplifier 112 (Step S6). The offset detector 830, according to the selection signal SS, detects the second current I2 to generate the second compensation code of the digital compensation signal SDC and stores the second compensation code in the register 870 (Step S7). The digital controller 810, according to the second compensation code, controls the second current digital-to-analog converter 850 to provide the compensation current for the band-pass output node NOBP (Step S8).

Then, the digital controller 810 turns ON the second switch 20 to couple the band-pass filtering amplifier 112 to the programmable-gain amplifier 113 (Step S9). The offset detector 830, according to the selection signal SS, detects the detection current ID to generate the third compensation code of the digital compensation signal SDC and stores the third compensation code in the register 870 (Step S10). The digital controller 810 controls the third current digital-to-analog converter 860 to provide the compensation current for the programmable-gain output node NOPG according to the third compensation code (Step S11).

While the invention has been described by way of example and in terms of preferred embodiment, it is to be understood that the invention is not limited thereto. Those who are skilled in this technology can still make various alterations and modifications without departing from the scope and spirit of this invention. Therefore, the scope of the present invention shall be defined and protected by the following claims and their equivalents.

What is claimed is:

1. A front-end amplifier circuit for receiving a biological signal, comprising:
   a signal channel, amplifying the biological signal to generate a detection current, wherein the signal channel comprises:
     a capacitive-coupled transconductance amplifier, amplifying the biological signal with a transconductance gain to generate a first current; and
     a band-pass filtering amplifier, filtering noise in the first current outside a bandwidth and amplifying the first current with a first current gain to generate a second current;

a programmable-gain amplifier, amplifying the second current with a second current gain to generate the detection current on a programmable-gain output node, wherein the second current gain is programmable; and an offset cancellation circuit, configured to cancel output offset currents of the capacitive-coupled transconductance amplifier, the band-pass filtering amplifier, and the programmable-gain amplifier.

2. The front-end amplifier circuit of claim 1, wherein the capacitive-coupled transconductance amplifier comprises:

a first input capacitor, coupled between a negative input node and a first node;

a second input capacitor, coupled between a positive input node and a second node, wherein the first input capacitor and the second input capacitor receive the biological signal by a way of AC-couple in a differential mode;

a first common-mode P-type transistor, configured to provide a common-mode voltage for the first node;

a second common-mode P-type transistor, configured to provide the common-mode voltage for the second node;

a first current source, configured to provide a first transconductance bias current;

a second current source, configured to provide a second transconductance bias current;

a first transconductance P-type transistor, wherein a source terminal receives the first transconductance bias current, and a gate terminal is coupled to the second node;

a second transconductance P-type transistor, wherein a source terminal receives the second transconductance bias current, and a gate terminal is coupled to the first node, wherein the first transconductance P-type transistor and the second transconductance P-type transistor are configured to the transconductance gain;

a linear resistor, coupled between the source terminal of the first transconductance P-type transistor and the source terminal of the second transconductance P-type transistor, wherein the linear resistor is configured to improve linearity of the transconductance gain;

a third transconductance P-type transistor, wherein a source terminal is coupled to a drain terminal of the first transconductance P-type transistor, and a gate terminal receives a transconductance bias voltage;

a fourth transconductance P-type transistor, wherein a source terminal is coupled to a drain terminal of the second transconductance P-type transistor, a gate terminal receives the transconductance bias voltage, and a drain terminal is coupled to a transconductance output node, wherein the transconductance output node outputs the first current;

a first transconductance N-type transistor, wherein a drain terminal and a gate terminal are both coupled to a drain terminal of the third transconductance P-type transistor;

a second transconductance N-type transistor, wherein a drain terminal is coupled to the transconductance output node, and a gate terminal is coupled to the gate terminal of the first transconductance N-type transistor;

a third transconductance N-type transistor, wherein a drain terminal and a gate terminal are both coupled to a source terminal of the first transconductance N-type transistor, and a source terminal is coupled to a ground; and a fourth transconductance N-type transistor, wherein a drain terminal is coupled to a source terminal of the second transconductance N-type transistor, a gate terminal is coupled to the gate terminal of the third transconductance N-type transistor, and a source terminal is coupled to the ground.

3. The front-end amplifier circuit of claim 1, further comprising:

a transimpedance amplifier, configured to amplify the detection current with a transimpedance gain to generate a voltage signal and to provide a driving capability for a coupled measurement system, wherein an amplified ratio of the biological signal converted into the voltage signal is a product of the transconductance gain, the first current gain, and the second current gain.

4. The front-end amplifier circuit of claim 1, wherein the band-pass filtering amplifier comprises:

a master band-pass current path, comprising a master band-pass bias current and configured to receive the first current;

a band-pass filter, AC-coupled to the master band-pass current path and filtering the noise of the first current outside the bandwidth to generate a filter signal; and a slave band-pass current path, comprising a slave band-pass bias current and generating the second current according to the filter signal, wherein the first current gain is a ratio of the slave band-pass bias current to the master band-pass bias current.

5. The front-end amplifier circuit of claim 4, wherein the master band-pass current path comprises:

a first master P-type transistor, wherein a source terminal receives a supply voltage, and a gate terminal is coupled to a drain terminal;

a second master P-type transistor, wherein a source terminal is coupled to the drain terminal of the first master P-type transistor, and a gate terminal and a drain terminal receive the first current;

a first master N-type transistor, wherein a gate terminal and a drain terminal are coupled to the drain terminal of the first master P-type transistor; and a second master N-type transistor, wherein a gate terminal and a drain terminal are coupled to a source terminal of the first master N-type transistor, and a source terminal is coupled to the ground.

6. The front-end amplifier circuit of claim 5, wherein the first master P-type transistor, the second master P-type transistor, the first master N-type transistor, and the second master N-type transistor are all operated in a sub-threshold region to reduce power consumption.

7. The front-end amplifier circuit of claim 5, wherein the slave band-pass current path comprises:

a first slave P-type transistor, wherein a source terminal is coupled to the supply voltage, and a gate terminal is coupled to a drain terminal;

a second slave P-type transistor, wherein a source terminal is coupled to a drain terminal of the first P-type transistor, and a drain terminal is coupled to a band-pass output node;

a first slave N-type transistor, wherein a gate terminal is coupled to a gate terminal of the second slave P-type transistor, and a drain terminal is coupled to the band-pass output node, wherein the gate terminal of the first slave N-type transistor receives the filter signal, and the band-pass output node outputs the second current; and a second slave N-type transistor, wherein a gate terminal and a drain terminal are coupled to a source terminal of the first slave N-type transistor, and a source terminal is coupled to the ground, wherein a ratio of transistor sizes of the slave band-pass current path to transistor sizes of the master band-pass current path is the first current gain.

8. The front-end amplifier circuit of claim 7, wherein the first slave P-type transistor, the second slave P-type transistor, the first slave N-type transistor, and the second slave N-type transistor are all operated in a sub-threshold region to reduce power consumption.

9. The front-end amplifier circuit of claim 7, wherein the band-pass filter comprises:
   a first differential-input amplifier, configured to generate a transconductance and comprising a first negative input node, a first positive input node, and a first output node, wherein the first negative input node is coupled to the first output node;
   a first coupling capacitor, coupled between the gate terminal of the second master P-type transistor and the first positive input node;
   a first bias P-type transistor, comprising channel resistance, wherein a source terminal receives the common-mode voltage, a drain terminal is coupled to the first positive input node, and a gate terminal is coupled to a first band-pass bias voltage;
   a low-pass capacitor, coupled between the first output node and the ground;
   a second differential-input amplifier, comprising a second negative input node, a second positive input node, and a second output node, wherein the second negative input node is coupled to the second output node, and the second positive node is coupled to the first output node;
   a third differential-input amplifier, comprising a third negative input node, a third positive input node, and a third output node, wherein the third negative input node is coupled to the third output node, and the third output node outputs the filter signal;
   a second coupling capacitor, coupled between the second output node and the third positive input node; and
   a second bias P-type transistor, providing a DC bias voltage for the third positive input node, such that the gate terminal of the second slave P-type transistor and the gate terminal of the first slave N-type transistor are biased to the DC bias voltage.

10. The front-end amplifier circuit of claim 9, wherein the bandwidth comprises a low-pass cut-off frequency and a high-pass cut-off frequency, wherein the transconductance and the low-pass capacitor determine the low-pass cut-off frequency, wherein the first coupling capacitor and the channel resistance determine the high-pass cut-off frequency.

11. The front-end amplifier circuit of claim 9, wherein the first bias P-type transistor is operated in a cut-off region, such that the channel resistance is at a high resistance level.

12. The front-end amplifier circuit of claim 9, wherein the offset cancellation circuit comprises:
   a digital controller, generating a first reset signal, a second reset signal, and a selection signal;
   a pseudo resistor reset module, shorting the first node and the second node to the common-mode voltage according to the first reset signal, and shorting the first positive input node to the common-mode voltage and the third positive input node to the DC bias voltage according to the second reset signal;
   an offset detector, sequentially detecting the first current, the second current, and the detection current according to the selection signal to generate a first compensation code, a second compensation code, and a third compensation code;
   a first current digital-to-analog converter, sinking or sourcing a first compensation current to the transconductance output node according to the first compensation code;
   a second current digital-to-analog converter, sinking or sourcing a second compensation current to the band-pass output node according to the second compensation code;
   a third current digital-to-analog converter, sinking or sourcing a third compensation current to the programmable-gain output node according to the third compensation code; and
   a register, configured to store the first compensation code, the second compensation code, and the third compensation code.

13. The front-end amplifier circuit of claim 12, wherein the offset cancellation circuit further comprises:
   a first switch, coupled between the capacitive-coupled transconductance amplifier and the band-pass filtering amplifier and turned OFF by the digital controller; and
   a second switch, coupled between the band-pass filtering amplifier and the programmable-gain amplifier and turned OFF by the digital controller.

14. The front-end amplifier circuit of claim 13, wherein when the first switch and the second switch are both turned OFF, the offset detector, according to the selection signal, detects the first current to generate the first compensation code, wherein
   when the first switch is turned ON and the second switch is turned OFF, the first current digital-to-analog converter sinks or sources the first compensation current to the transconductance output node, and the offset detector, according to the selection signal, detects the second current to generate the second compensation code, wherein
   when the first switch and the second switch are both turned ON, the first current digital-to-analog converter sinks or sources the first compensation current to the transconductance output node, the second current digital-to-analog converter sinks or sources the second compensation current to the band-pass output node, and the offset detector, according to the selection signal, detects the detection current to generate the third compensation code.

15. The front-end amplifier circuit of claim 13, wherein the offset detector further comprises:
   a signal converter, converting an input current into an offset voltage;
   a selector, sequentially selecting one of the first current, the second current, and the detection current to be the input current according to the selection signal; and
   a comparator, comparing the offset voltage with the common-mode voltage to generate a digital compensation signal, wherein the digital controller determines the first compensation code, the second compensation code, and the third compensation code according to the digital compensation signal.

16. The front-end amplifier circuit of claim 3, further comprising:
   another signal channel, receiving and amplifying another biological signal to generate another detection current; and a multiplexer, providing either one of the detection current and the another detection current for the transimpedance amplifier.

* * * * *